(12) United States Patent
Noakes et al.

(10) Patent No.: US 6,326,062 B1
(45) Date of Patent: Dec. 4, 2001

(54) SPRAYING DEVICES

(75) Inventors: Timothy James Noakes; Andrew Jefferies, both of Clwyd; Maurice Joseph Prendergast, Runcorn; Michael Leslie Green, Clwyd, all of (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/732,256
(22) PCT Filed: Apr. 24, 1995
(86) PCT No.: PCT/GB95/00915
§ 371 Date: Mar. 20, 1997
§ 102(e) Date: Mar. 20, 1997
(87) PCT Pub. No.: WO95/29758
PCT Pub. Date: Nov. 9, 1995

(30) Foreign Application Priority Data

Apr. 29, 1994 (GB) ................................................ 9408570
Oct. 4, 1994 (GB) ................................................ 9419988

(51) Int. Cl.$^7$ ....................................................... B05D 1/04
(52) U.S. Cl. ........................... 427/475; 427/483; 118/620; 118/624; 118/627; 118/629; 239/704; 239/707; 239/708

(58) Field of Search .................................... 118/620, 621, 118/624, 625, 627, 629, 679, 635; 427/421, 457, 458, 472, 475, 483; 239/690, 704, 706, 707, 708

(56) References Cited

U.S. PATENT DOCUMENTS 3,677,470 * 7/1972 Probst et al. ...................... 239/690
4,854,506 * 8/1989 Noakes et al. ..................... 239/707

FOREIGN PATENT DOCUMENTS

| 0 120 633 | 10/1984 | (EP) . |
| 0 441 501 | 8/1991 | (EP) . |
| 0 501 725 | 9/1992 | (EP) . |
| 0 523 963 | 1/1993 | (EP) . |
| 1 004 267 | 9/1965 | (GB) . |
| 94 13063 | 6/1994 | (WO) . |

* cited by examiner

Primary Examiner—Laura Edwards
(74) Attorney, Agent, or Firm—Leonard W. Lewis

(57) ABSTRACT

An electrostatic spraying device for use in spraying inter alia personal care and personal hygiene products comprises an outlet (94) from which the product issues in the form of an electrostatically charged spray and a control member (60, 60a) for attenuating the potential gradient in the vicinity of the outlet (94) to such an extent that spraying is suppressed until the device is brought to within a predetermined distance from a site to be spayed.

18 Claims, 1 Drawing Sheet

SPRAYING DEVICES

This application is a 371 of PCT/GB95/00915, filed Apr. 24, 1995.

This invention relates to electrostatic spraying devices of the kind comprising an outlet, means for supplying an electrostatically sprayable material to the outlet and high voltage circuitry arranged so that, in use, the material issuing from the outlet forms an electrostatically charged spray.

The present invention is concerned with a device of this kind which affords improved control over spraying, particularly for applications requiring localised deposition of the material being sprayed. Typical applications where such control is required are those involving the application of personal hygiene, personal care, cosmetic, skin treatment and hair care products to the parts of the body—eg eye make-up, fingernail varnish etc.

EP-A-523963 makes reference to deposition localisation of benefit or treatment agents to the hair and/or scalp and discloses a specific embodiment in the form of a brush provided with liquid delivery elements and means for electrostatically charging the liquid. Reference is also made in this patent to an alternative liquid spraying unit with electrostatic charging of the liquid in which proximity sensing means is provided for allowing or causing the unit to operate only when the delivery means are suitably close to the intended target, namely the hair or the scalp. No specific details are disclosed as to how such proximity sensing is to be achieved.

In our prior EP-A-120633, there is described an electrostatic spraying device for use in various applications, including spraying of personal hygiene products, cosmetics, skin treatment formulations and perfumes. In this device, a voltage is developed between the spraying nozzle and earth which is of sufficient magnitude that spraying can be effected at a distance of 2 cm from an earthed surface. Reference is made to developing a field strength at the nozzle such that spraying ceases when the nozzle is not more than a distance of 15 cm away from the earthed surface.

In our prior EP-A-441501 there is described an electrostatic spraying device of the above kind in which an annular shroud of electrically non-conducting material material is mounted adjacent the nozzle such that the shroud becomes electrically charged during use of the apparatus, the shroud being either adjustable or there being a number of different interchangeable shrouds so that by adjustment of the shroud or by interchanging one shroud for another, the shape of the spray may be controlled.

Prior EP-A-501725 discloses an electrostatic spraying device for use in spraying low resistivity liquids such as aqueous, alcohol and aqueous/alcohol based liquids used in personal care products such as deodorants, anti-perspirants, scents and hair sprays. Reference is made to arrangements for attenuating the potential gradient in the vicinity of the orifice of the spraying nozzle with the aim of achieving sufficient potential gradient to promote necking of the liquid ligaments produced from the orifice while reducing the very steep gradients normally associated with pointed nozzle tips which, with low resistivity liquids, tend to give rise to corona discharge from the liquid jet.

According to one aspect of the present invention there is provided a method of applying an agent in spray form to the body by electrostatically spraying the agent on to a selected site of the body using a device having (i) a dispensing outlet from which the agent issues to form an electrostatically charged spray by the application of high voltage to the agent from a voltage source housed within the device and (ii) a portion projecting forwardly of the dispensing outlet in the direction of spraying, on which a potential is established in use to suppress spraying until the forward extremity of the device is brought within a predetermined distance from an earthed target, said method including addressing the body site to be sprayed with the device in such a way that the spraying outlet is sufficiently close to the body site to overcome the suppression of spraying imparted by the potential established on said forwardly projecting portion and thereby allow application of spray to the selected site.

Usually the device will be constructed and arranged so that spraying is suppressed until the spraying outlet is within a range of 20 cm or less (more preferably 15 or even 10 cm) from an earthed target.

Typically the agent applied will comprise be of a cosmetic nature such as personal care products, eg deodorants, antiperspirants, anti-bacterials, perfumes, hair sprays, fresheners, moisturisers and conditioners; and beautifying cosmetics such as lip colouring materials, mascaras, eye shadows, foundation formulas, artificial tanning materials, nail varnishes, nail polishes, nail hardeners etc.

According to a second aspect of the present invention there is provided a device comprising a spraying outlet, means for supplying electrostatically sprayable material to the outlet and high voltage circuitry arranged so that, in use, the material issuing from the outlet forms an electrostatically charged spray, characterised by the provision of a control member on which a voltage of the same polarity as that applied to the material to be sprayed is developed in use, the control member being located forwardly of the outlet in the direction of spraying and arranged in such a way as to attenuate the electric field in the vicinity of the outlet so that spraying from the outlet is suppressed until the forward extremity of the control member is brought within a range of no more than 20 cm from an earthed target to be sprayed.

Thus, in contrast with EP-A-441501 and EP-A-501725 which are respectively concerned with controlling the shape of the spray and with ligament formation, the present invention is concerned with controlling the potential gradient in the vicinity of the outlet so that spraying, and hence deposition of the material, is suppressed until the forward extremity of the control member is brought within a range of no more than 20 cm (more preferably no more than 15 cm, and in many cases no more than 10 cm) from an earthed target.

In one embodiment of the invention the control member comprises a control member of non-conducting material which surrounds the outlet and collects electrical charge leaking from the outlet during the initial application of voltage for spraying of the material (eg. stray corona discharge from the outlet). This approach may be used where the arrangement is such that the time interval between initial application of the spray inducing voltage and the onset of actual spraying allows development of a spray suppressing potential on the control member when the forward extremity of the control member is more than 20 cm from the earthed target.

In an alternative embodiment, the control member may be composed of a semi-insulating material which is coupled to a source of high voltage (preferably said high voltage circuitry) forming part of the device and has sufficient conductivity to permit a potential to be established at a location forwardly of the outlet which is of the same polarity as that applied to the liquid emerging at the outlet.

Thus, the control member serves to prevent spraying from the outlet when the device is remote from the target. In other words, even though the spray inducing voltage may be sufficient in the absence of the control member to allow spraying over a wide range of outlet/target distances extending well beyond 20 cm, the presence of the control member in effect modifies the potential gradient in the immediate vicinity of the outlet to such an extent that the field strength only becomes sufficient to generate electrostatic spraying from the outlet if the latter is within about 20 cm or less from an earthed target. In this way, even with the high voltage generating circuitry operational, the provision of the control member prevents issue of material from the outlet and hence spraying until the device is brought into dose proximity with the surface, eg the face, to be sprayed thereby ensuring deposition of the sprayed material on to a localised surface area.

In some applications, it may be desirable for the control member to be arranged so that spraying is suppressed until the control member is no further than 10 cm or even less (no more than 5 cm, eg 1 to 2 cm), and hence until the outlet is about 10 cm/5 cm or less, away from the target before electrostatic spraying can commence. Typical applications in which the device of the invention may be used include those cosmetic/personal care applications mentioned previously and also include the spraying of medical/therapeutic product formulations to parts of the body, eg. the face, hair, eyes, nose or mouth.

The material to be sprayed will be one which has suitable properties, eg resistivity and flow properties, to allow it to be sprayed electrostatically. Often the material to be sprayed will be in the form of a solution; however, we do not exclude the possibility of the active material being in other forms such as a finely divided form, eg a suspension of solid particles of the active material in a liquid where the liquid may be an active component of the formulation or merely a vehicle for the solid particulate material. Usually the application of the high voltage to the material at the outlet will be via the body of material itself. For instance, the material may be supplied to the outlet from a storage volume within the device and the high voltage may be applied to the material in the storage volume or at some other point in the flow path between the storage volume and the outlet and conducted through the body of material to the material present at the outlet.

In general where the material to be sprayed is in the form of a liquid, the high voltage circuitry will have the effect of causing the propulsion of one or more filaments or ligaments of liquid from the outlet, which ligament(s) break up into electrostatically charged droplets.

In a preferred embodiment of the invention, the outlet is mounted in fixed relation to the body of the device and the control member is in the form of an annular shroud mounted on the device body in substantially concentric relation with, and usually in fixed relation to, the outlet. The control member and the outlet may however be adjustable with respect to one another in the direction of spraying.

Where the outlet and/or the control member is adjustable, preferably the limits of adjustment are such that the control member, over substantially its full range of adjustment, has its forward extremity (as considered in the direction of spraying) located forwardly of the outlet. The arrangement is conveniently such that, in all positions of relative adjustment, spraying is suppressed until the forward extremity of the control member is within a distance of 20 cm (more preferably 10 cm) from an earthed target.

In general, the means for supplying the material to be sprayed to the outlet will be a passive feed means, such as a liquid capillary feed, as opposed to a positive feed arrangement requiring moving components.

In one embodiment, the outlet is constituted by a capillary structure which acts as a passive feed means effective to draw liquid from a reservoir thereof to the tip of the structure by capillary action, the tip constituting the outlet from which the liquid issues and breaks up into a spray under the influence of the applied voltage. Typically the capillary structure comprises a wicking material as described for example in our prior EP-A-120633 and International Application No. WO93/06937, the entire disclosures of which are incorporated herein where the context admits.

Preferably the device does not incorporate any structure forming a field intensifying electrode, ie. the outlet is so arranged that the field strength produced when liquid is present at the outlet is substantially independent of any low potential influence from from the device.

In a preferred embodiment of the invention, the device is suitable for hand held use and comprises a housing accommodating the high voltage circuitry and including sections for receiving a power source such as a battery or battery pack and for receiving a reservoir of material to be sprayed. The device preferably includes a user operable trigger or pushbutton, conveniently operable by one of the fingers gripping the hand grip portion, for selectively connecting and disconnecting the outlet to the high voltage circuitry. The control member may be mounted slidably on the body so that the operator can adjust it relative to the outlet.

The material to be sprayed is advantageously contained in a cartridge which is removable from the device for replacement purposes.

The device is typically designed to produce a spraying rate of up to 0.2 cc/min, often no more than 0.1 cc/min and the voltage generator will normally have a voltage output, at the current drawn during normal spraying, no greater than 14 kV, typically no greater than 12 kV.

Liquid formulations for spraying using the device of the invention will usually have a resistivity at 25° C. of about $10^4$ to $10^{12}$ ohm.cm (more usually about $10^5$ to about $10^{10}$ ohm.cm) and a viscosity at 25° C. of about 0.1 to about 50000 mPas (more usually about 0.1 to about 10000 mPas, preferably about 0.5 to 5000 mPas).

The invention also encompasses a method of applying to the body a formulation by electrostatically spraying the formulation by means of a device in accordance with said second aspect of the invention where such formulation is constituted by inter alia a personal care product, a personal hygiene product, a cosmetic, a perfume or fragrance, a benefit or treatment agent for the hair or scalp, a skin treatment agent, an agent for oral, ocular or nasal application, etc.

BRIEF DESCRIPTION OF THE DRAWINGS

The invention will now be described by way of example with reference to the accompanying drawings, in which.

Figure 1:
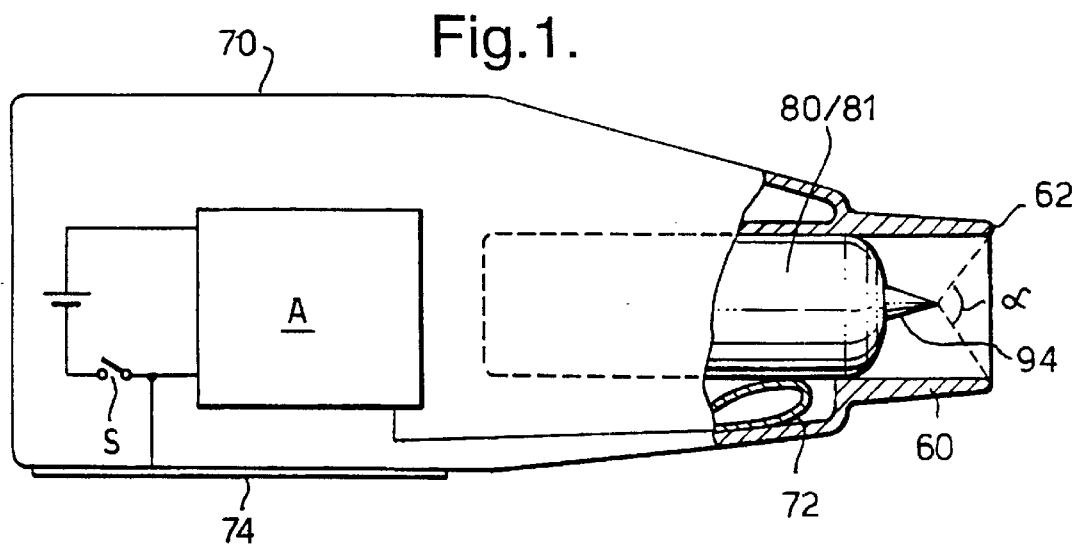
FIG. 1 is a schematic view of a device for spraying for example cosmetic formulations.
Figure 2:
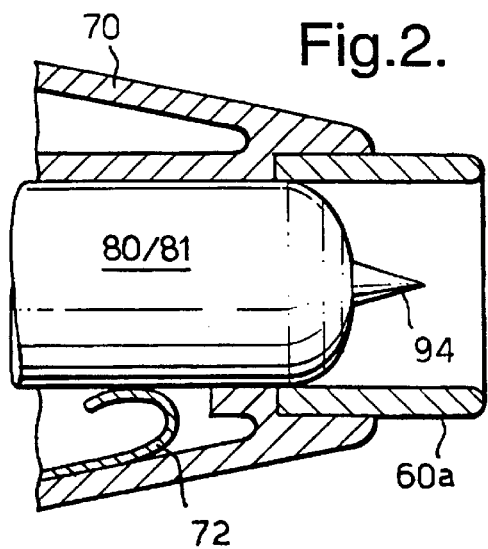
FIG. 2 is fragmentary view showing a modification.
Figure 3:
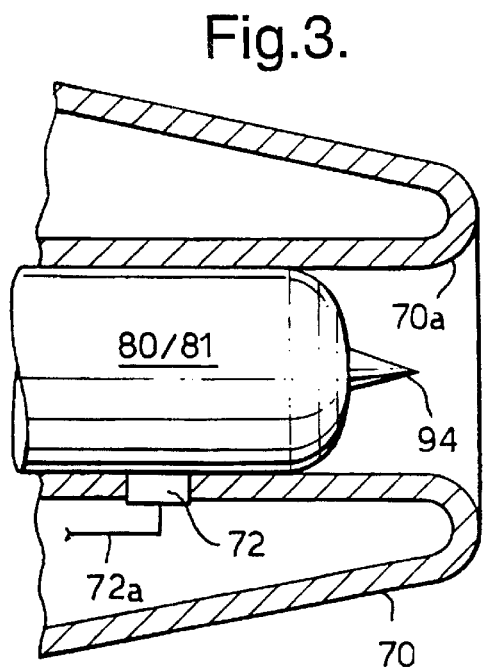
FIG. 3 is fragmentary view showing a further modification.

Referring to the drawing, the device shown is generally constructed and arranged to operate in the same manner as the device described in connection with FIGS. 5 to 9 of EP-A-120833 and reference should be made to the latter for further details, including details of the properties of typical formulations to be sprayed by the device. A liquid composition to be sprayed is contained within a cartridge 80/81 which may enclose a wad or strip of porous material impregnated with the liquid for passive feed to the tip of a nozzle 94 constituted by a porous wick-type element extending into the cartridge to enable liquid to be fed by capillary action to the tip of the nozzle independently of the orientation of the device, the tip of the nozzle constituting the dispensing outlet of the device. The cartridge is removably inserted into the housing 70 of the device which is fabricated from an electrically insulating material and accommodates the battery powered high voltage generating circuitry A of the device operation of which is controlled by switch S, the high voltage being coupled to the nozzle tip via contact 72 and via the cartridge casing which may be conductive or partly conductive for this purpose or, if made of an insulating material, may have a conductive contact or wall portion through which the voltage is coupled to the body of liquid within the cartridge and thence to the outlet constituted by the nozzle tip.

The nozzle 94 terminates in a tip forming a spraying edge having a profile which may take any of the forms disclosed in EP-A-120633 or International Application No. WO93/08937, eg chisel-shaped or formed with a plurality of teeth from which the liquid is projected in use in the form of a plurality of ligaments per tooth, the ligaments being formed and projected preponderantly under the influence of electrostatic forces and thereafter breaking up into charged droplets. The nozzle may be fabricated from a strip cut from a sheet of material having open porosity, eg an open celled foam material, and assembled to the cartridge 80/81 in the manner disclosed in International Application No. WO93/06937.

Alternatively the nozzle may comprise a rod-like length of porous, open celled material terminating in a tip from which the liquid is projected to create the spray. In this instance, the material may be a plastics wicking material having an open celled structure within an outer skin, produced for instance by extrusion techniques. The spraying tip of the rod-like nozzle may be appropriately contoured as disclosed in for example EP-A-120633 and International Application No. WO93/06937.

One convenient configuration for the tip is obtained by cutting the rod-like length to produce an end face which extends obliquely between diametrically opposite sides of the rod so as to impart to the rod an asymmetric configuration such that the rod has an acute angled leading extremity at one side thereof from which spraying is favoured. The included angle between the oblique end face and an axial generatrix of the outer periphery is typically in the range of 30 to 60° (preferably 40 to 50°). Such a tip configuration is suitable for nozzles fabricated from a porous plastics wicking material comprising an open celled structure within an impermeable outer peripheral skin. The outer skin need only be present in the vicinity of the tip of the nozzle. At other locations, the skin may be removed at least in part so as to expose the open celled structure for liquid ingress particularly over the length of the rod immersed in the liquid to be fed to the tip by the wicking action. Preferably the cross-sectional configuration of the rod is such that the oblique cut intersects the outer periphery of the rod to produce a sharply curved edge at which an intense electric field can be developed and from which spraying is therefore favoured. Usually therefore the rod-like nozzle will be produced with a round section. However, we do not exclude the possibility of using other geometrical cross-sections which can be obtained readily by extrusion techniques.

The liquid composition contained in the cartridge 80/81 typically contains one or more volatile components, for example a moderately volatile scent oil and an alcohol (highly volatile), the formulation typically having a resistivity in the range of $1 \times 10^5$ to $1 \times 10^7$ ohm cm. The rate of delivery of the liquid composition using a porous wick-type nozzle is usually ultra-low, eg of the order of 1 $\mu$l/min or less, which is desirable for many forms of personal care and hygiene products. However, if the nozzle terminates in a point or bullet head configuration, the rate of delivery may tend to be unacceptably slow. The rate of delivery can be increased by providing a nozzle that produces multiple ligaments, eg by configuring the nozzle tip 94 with a toothed profile or an asymmetric leading extremity as mentioned above so that the liquid is projected from the nozzle as a number of ligaments under the influence of the electrical field, each ligament breaking up into a spray of charged droplets. The droplets produced are attracted in use to an earthed object such as the face when used to apply cosmetic forumulations. An earth return circuit is provided through the operator via a pad 74 which is connected to the internal circuitry. The pad 74 may be conductive or of semi-conductive material and may be mounted on the housing of the device or form an integral part of the housing.

The housing 70 is provided with a control member in the form of an annular shroud 60 also formed of insulating material. The forward extremity of the control member, ie the shroud in this embodiment, also constitutes the forward extremity of the device as a whole. In initial operation of the device small amounts of charge accumulate on the shroud especially at the outer edge 62 of the shroud and the interior surface of the shroud immediately adjacent the outer edge 62. As the shroud is insulating, e.g. being made of non conducting material, e.g. Tufnol, ABS, polypropylene, polyethylene, polyvinyl chloride, acrylic, polycarbonate, acetal, and is supported on the insulating housing 70, leakage is sufficiently slow as to leave the shroud charged. The charge on the edge is of the same polarity as the voltage applied to the liquid emerging from the tip of the nozzle. The shroud 60 can thus be used to control the spray in a manner to be described below.

As illustrated, the shroud 60 may be integral with the housing 70. Alternatively it may be mounted on the housing as a separate component and may be adjustable in the axial direction so that the position of the edge 62 can be varied with respect to the tip of the nozzle.

A feature of the shroud in the illustrated embodiment is that it has the effect of simulating a more obtuse nozzle which tends to give a more regular spraying direction than an acute nozzle. In the case of an acute nozzle (in the absence of a shroud), there is a greater likelihood of the spray deflecting away from the axis of the nozzle. Another feature of the shroud is that it tends to charge up to a greater extent as the background corona increases (for example as the nozzle is moved closer to the target) and the shroud therefore tends at least partly to nullify the increased tendency for corona discharge. In this way, it is possible to approach a target and avoid undesirable corona effects by designing the device with the shroud located beyond the tip of the nozzle. Without the shroud, it would still be possible to approach the target without undesirable corona effects but only by reducing the magnitude of the voltage output of the HT generator.

The control member constituted by the shroud 60 is arranged to prevent spraying until the nozzle is located proximate the target to be sprayed. This can be achieved for a given material to be sprayed by appropriate selection of the operating voltage (ie the voltage applied to the liquid emerging from the tip of the nozzle), dimensioning of the shroud and relative positioning of the nozzle tip and the forward extremity of the shroud. This is implemented for a suitable operating voltage by locating the forward extremity 62 a substantial distance forwardly of the nozzle tip to such an extent that the potential (which will be of the same polarity as the voltage applied to the nozzle) produced at the extremity 62 by charge leakage of the nozzle substantially modifies the potential gradient in the immediate vicinity of the nozzle.

In this way, even with switch S closed so that the voltage generator A is operative, spraying from the nozzle can be quenched until the nozzle 94 and hence the shroud is brought to within a predetermined distance from an earthed target such as the user's face. When the shroud approaches the earthed target, some of the potential existing on the shroud may be lost to earth as a result of corona discharge, thereby allowing the nozzle to commence spraying. Where the shroud is fixed with respect to the nozzle, for use in the spraying of cosmetic and other formulations to the face the arrangement may be such that the angle a (being the angle subtended by the extremity 62 at the point of intersection between the nozzle axis and a plane which is normal to the axis and passes through the leading extremity or extremities of the nozzle tip) is less than that corresponding to the angle at which the control member ceases to be effective to quench the spray when the forward extremity of the control member and hence the device is at a distance of say 10 cm, more preferably 5 cm, from the target, eg the user's face.

Where the shroud is mounted on the device housing for adjustment relative to the nozzle, the range of adjustment is conveniently such that, over the range of adjustment of the shroud, the angle $\alpha$ is less than the angle at which spray quenching ceases (eg at a distance of 10 cm, more preferably 5 cm, from an earthed target).

Instead of the shroud being composed of an insulating material, it may instead be composed of a semi-insulating material as disclosed in International Application No. WO94/13063 (a suitable material being one with a bulk resistivity in the range of $10^{11}$–$10^{12}$ ohm.cm such as "Hytrel" grade 4778 available from DuPont Corporation), and connected to the output high voltage generator whereby a voltage of the same polarity and substantially the same magnitude as that applied to the material to be sprayed is established on the forward extremity of the shroud to effect suppression of spraying. FIG. 2 illustrates an embodiment of this aspect of the invention. In this instance, the shroud 60*a* is produced as separate component from the housing 70 and is mounted on the housing so as to encircle the nozzle 94 with the forward extremity of the shroud located forwardly of the nozzle tip. The housing 70 is fabricated from an electrically insulating material while the shroud is fabricated from a semi-insulating material such as "Hytrel" grade 4778 and is electrically connected to the high voltage output of the voltage generating circuitry A by contact with the conductive casing of the cartridge 80/81, or a conductive track on the casing where the latter is not conductive, which in turn is coupled to the high voltage output of circuit A by contact 72. A voltage of the same polarity and of substantially the same magnitude as that applied to the material to be discharged is rapidly established at the forward extremity of the shroud 60*a* in response to energisation of the high voltage circuitry. In this manner, for liquids within a given range of resistivities, by appropriate selection of the applied voltage and appropriate positioning of the shroud, suppression of spraying may be secured until the device is brought sufficiently close to the target to be sprayed.

Referring to FIG. 3, in this embodiment the control member for controlling suppression of spraying is constituted by the forward end 70*a* of the housing 70 which is fabricated from an electrically insulating material and is contoured so as to extend beyond the tip of the nozzle 94 when the cartridge is correctly inserted into the housing. The high voltage output of the generator is applied to the nozzle tip via the body of liquid in the cartridge via contact 72 and lead 72*a*. In this case, the voltage necessary to attenuate the field gradient in the vicinity of the nozzle tip is developed on the forward end of the housing 70 by charge leaking from the nozzle, eg by way of corona charging, and depositing on the forward end of the housing where the charge tends to remain since mobility of the charge is low by virtue of the insulating properties of the material from which the housing is fabricated. In a modification, the housing 70 may be similarly contoured but the forward end thereof may be fabricated from a semi-insulating material and connected by any suitable means to the high voltage output of the generator so as to establish a voltage of the same polarity and similar magnitude to that applied to the nozzle 94.

The devices described above may also incorporate other features. For example, it may employ a bipolar voltage generating arrangement for the purposes disclosed in our prior EP-A-488735, EP-A-48736 or International Application No. WO94/13063, the entire disclosures of which are incorporated herein by this disclosure. Similarly, with regard to the possible electrostatically sprayable formulations that may be sprayed, examples may be found in EP-A-523960, EP-A-523961, EP-A-523962, EP-A-523963 and EP-A-523964, the entire disclosures of which are incorporated herein by this reference where the context admits.

What is claimed is:

1. A method of applying an agent in spray form to a body comprising electrostatically spraying the agent on to a selected site of the body using a device having (i) a dispensing outlet from which the agent issues to form an electrostatically charged spray by the application of high voltage to the agent from a voltage source housed within the device and (ii) a portion projecting forwardly of the dispensing outlet in the direction of spraying, on which a potential is established in use to suppress spraying until the forward extremity of the device is brought within a predetermine distance from an earthed target, said method including addressing the body site to be sprayed with the device in such a way that the spraying outlet is sufficiently close to the body site to overcome the suppression of spraying imparted by the potential established on said forwardly projecting portion and thereby allow application of spray to the selected site.

2. A method as claimed in claim 1 in which the device is constructed and arranged to operate in such a way that suppression of spraying is not overcome until the dispensing outlet is within 20 cm from an earthed target.

3. A method as claimed in claim 1 in which the device is constructed and arranged to operate in such a way that suppression of spraying is not overcome until the spraying outlet is within 10 cm from an earthed target.

4. An electrostatic spraying device comprising a spraying outlet, means for supplying electrostatically sprayable material to the outlet and high voltage circuitry arranged so that, in use, the material issuing from the outlet in a direction away from said outlet forms an electrostatically charged spray, said spray having a voltage and a polarity and wherein an electric field forms in the vicinity of the outlet during use, further comprising a control member on which a voltage of the same polarity as that applied to the material to be sprayed is developed in use, the control member being located forwardly of the outlet in the direction of spraying and arranged in such a way as to attenuate the electric field in the vicinity of the outlet so that spraying from the outlet is suppressed until the forward extremity of the control member is brought within a range of no more than 20 cm from an earthed target to be sprayed.

5. A device as claimed in claim 4 in which the means for supplying said material to the outlet is operable to feed the material passively.

6. A device as claimed in claim 4 in which the control member comprises a non-conducting material which surrounds the outlet and develops said voltage of the same polarity by collection of stray electrical charge from the outlet during an initial application of voltage for spraying of the material.

7. A device as claimed in claim 4 wherein said device further comprises a source of high voltage and wherein the control member is composed of a semi-insulating material which is coupled to the source of high voltage, said semi-insulating material having sufficient conductivity to permit a potential to be established at a location forwardly of said outlet which is of the same polarity as that applied to the material emerging at the outlet.

8. A device as claimed in claim 4 in which the control member is so arranged that spraying is suppressed until the control member is no more than 15 cm away from an earthed target.

9. A device as claimed in claim 4 in which the control member is so arranged that spraying is suppressed until the control member is no more than 10 cm away from an earthed target.

10. A device as claimed in claim 4 in which the control member is so arranged that spraying is suppressed until the control member is no more than 5 cm away from an earthed target.

11. A device as claimed in claim 4 wherein voltage circuitry is coupled to the spraying outlet.

12. A device as claimed in claim 4 in which the material to be sprayed comprises a liquid solution or a suspension of solid particles in a liquid vehicle.

13. A device as claimed in claim 4 in which the outlet is constituted by the tip of a length of porous wicking material.

14. A device as claimed in claim 13 in which the wicking material comprises a rod-shaped length of wicking material having one end face thereof extending obliquely between diametrically opposite sides of the rod-shaped length of wicking material so as to impart to the rod an asymmetric configuration such that the rod-shaped length of wicking material has a leading extremity at one side thereof from which spraying is favoured.

15. An electrostatic spraying device comprising casing housing a high voltage generator, a dispensing outlet from which an electrostatically sprayable material is sprayed in use wherein when sprayed said spray had a voltage and a polarity, reservoir for containing material to be sprayed in bulk wherein during use said reservoir contains bulk material to be sprayed, a passive feed arrangement for supplying said material to the dispensing outlet, means coupling the high voltage output of the generator to the bulk material so that the voltage is conducted through the bulk material to the material present at the dispensing outlet whereby the material issuing from the outlet under the influence of an applied voltage forms an electrostatically charged spray wherein an electric field forms in the vicinity of the outlet during use, characterized by the provision of a control member on which a voltage of the same polarity as that applied to the material to be sprayed is developed in use, the control member being located forwardly of the dispensing outlet in the direction of spraying and arranged in such a way as to attenuate the electric field in the vicinity of the outlet so that spraying from the outlet is suppressed until the forward extremity of the control member is brought within a range of no more than 15 cm from an earthed target to be sprayed.

16. A device as claimed in claim 15 wherein the control member attenuates the electric field such that spraying from the outlet is suppressed until the forward extremity of the control member is brought within a range of no more than 10 cm from an earthed target to be sprayed.

17. A device as claimed in claim 15 wherein the control member attenuates the electric field such that spraying from the outlet is suppressed until the forward extremity of the control member is brought within a range of no more than 5 cm from an earthed target to be sprayed.

18. A device as claimed in claim 15 in which the passive feed arrangement comprises a liquid wicking element which terminates in a tip constituting the dispensing outlet.

* * * * *